United States Patent [19]

Williams

[11] Patent Number: Plant 5,910

[45] Date of Patent: Mar. 24, 1987

[54] MINIATURE ROSE PLANT NAMED MINRCO

[76] Inventor: Ernest D. Williams, 1510 Lebanon Ave., Dallas, Tex. 75208

[21] Appl. No.: 728,664

[22] Filed: Apr. 29, 1985

[51] Int. Cl.[4] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by the pink and white bi-color coloration of the very double flowers and by the profusion of bloom.

1 Drawing Figure

The present invention relates to a new and distinct variety of hardy, dwarf, bush type rose plant of the miniature class; the variety being primarily characterized—as to novelty—by the distinctive bi-color coloration of the flowers, being quite red on upper surface and lighter (pink to yellowish white) on lower surface, the general color effect being similar to Over The Rainbow (miniature—U.S. Plant Pat. No. 3,472) but the pink/red color is deeper.

The variety is further characterized by:

An abundance of bloom, with flowers usually borne singly.

Slight fragrance.

A plant which is vigorous, of bushy upright shape with semi-glossy, small foliage, with pointed leaflets; the buds and flowers being similar in form and size to Over The Rainbow (miniature—U.S. Plant Pat. No. 3,472).

The plant, which has a normal height of about 30 cm or more, can easily be maintained at lesser height by occasional trimming.

A plant which grows and blooms satisfactorily outdoors; is good for growing in pots; and provides excellent garden decoration as well as cut flowers.

The present variety of miniature rose was originated by me at my nursery located at Dallas, Tex., under conditions of careful control and observation, as a cross between Little Darling (a floribunda—U.S. Plant No. 1,581, expired) as the seed parent and Over The Rainbow (miniature—U.S. Plant Pat. No. 3,472) as the pollen parent.

Subsequent to origination of the variety I successfully reproduced it, at my nursery located as aforesaid, by cuttings; the reproductions having run true in all respects.

The color photograph illustrates the variety, including the foliage, bud and flower.

Referring now specifically to the new and distinct variety of miniature rose plant, the following is a detailed description thereof in outline; all major color plate identification being by reference to the British Colour Council Horticultural Color Chart, except where common terms of color definition are employed.

Type: Hardy; dwarf; bushy; upright; seedling; outdoors; cut flowers; garden decoration; potted plant.

Class: Miniature. Variety identifications: Minrco, Commercial synonym: Cheryl's Delight.

Flowers borne: Usually singly on slender wirey stems.

Quantity of bloom: Abundant.

Bud:

*Peduncle.*—Medium to long length; slender but sturdy; erect; medium green, sometimes tinted bronze (outdoors); hairs — few.

*Before calyx breaks.*—Size — small. Form short; pointed with several foliaceous apendages and few or no tiny hairs on surface of bud; with foliaceous parts extending beyond the tip of the bud equal to one-half or less of its length. Color — medium green, occasionally tinted with bronze (outdoors).

*As calyx breaks.*—Color — near white, often tinted reddish near tip.

*Opening.*—Opens well in all weather.

Bloom:

*Size when fully open.*—Small, averaging about 30 mm (1¼").

*Petalage very double.*—Averaging about 40 petals, arranged regularly plus sometimes several small petaloids.

*Form.*—High centered, with petals reflexing loosely outward, and later at maturity, rolled loosely outward and downward. Open flowers may show stamens.

Petals: Fairly thick; satiny on inside and on outside surface.

*Shape.*—Outside petals, broad lanceolate — almost round; intermediate — broad lanceolate with small acute tip; intermediate — lanceolate with short acute tip.

Color: Newly opened flower from a plant grown outdoors (1984 season), Dallas, Tex.

*Outside surface.*—Near white or pinkish, with sometimes a yellowish cast on most of petal, shading or blending into deeper pink near petal edges.

*Inside surface.*—Near Geranium Lake 20/1 or darker.

Note: This color can appear both lighter or darker depending upon the light intensity, time of year and even fertility of soil. Also, the blending and/or veining of color and the sheen of petal surface can make the red color to appear darker. Generally, for this variety, the red color is darker when grown outdoors and lighter when grown in semi-shade or in greenhouse.

Intermediate petal:

*Outside surface.*—Similar to outside petal.

*Inside surface.*—Similar to outside petal.

Inner petal:

*Outside surface.*—Same as intermediate petal.

*Inside surface.*—Same as intermediate petal.

*General color effect; newly opened flowers.*—Pink (near red).

*Three days open.*—Color similar to newly opened flowers but less brilliant.

*Behavior.*—Opens well in all weather. Color becomes less brilliant as flowers age.

*Flower longevity* (*May* 1984).—Plant in pot 6–8 days or longer. Cut flowers at living room temperature 4–5 days or longer.

Reproductive organs:

*Stamens.*—Few.

*Filaments.*—Varying length, yellow.

*Anthers.*—Yellow (if present).

*Pollen.*—Usually none.

*Pistils.*—Average number.

*Styles.*—Fairly even; medium to short length; bunched; color — pale greenish.

*Ovaries.*—All enclosed in calyx.

*Hips.*—None.

*Sepals.*—Permanent; spear shaped; recurved against peduncle.

*Seed.*—None.

Foliage:

*Leaves.*—Compound of five (sometimes three or seven) leaflets; fairly small; leathery; semi-glossy to matt.

*Leaflets.*—Shape: broad, nearly oval, apex acute, base rounded or rounded acute. Margin serrate. Color: medium to dark (sometimes bronzy) green; new growth — normal (medium green) — often tinted reddish. Rachis: medium strength; upper side may have a few tiny short prickles or hairs, grooved; underside sparsely thorny with few or no tiny prickles. Stipules: medium length, narrow points which turn out usually at about 45 degrees or less.

Growth:

*Habit.*—Dwarf; bushy; upright; much branched.

*Growth.*—Free vigorous; internodes short.

*Canes.*—Medium; slender; sturdy.

*Main stems.*—Color; medium green.

*Thorns.*—Few; slender, hooked slightly downward; color; tan. Prickles — none. Hairs — none.

*Branches.*—Color; medium green, Thorns: few; medium length; slender; nearly straight, inclined downward. Medium oval base. Prickles: none. Hairs: none.

The miniature rose plant and its flowers as herein described may vary in slight detail due to climatic, soil and cultural conditions under which the variety may be grown; the present decription being of the variety as grown at Dallas, Tex.

The following is claimed:

1. A new and distinct variety of miniature rose plant of hardy, dwarf, bushy, upright, much branched habit, substantially as illustrated and described, characterized by buds and flowers of deep pink to medium red (with pink/yellowish reverse), being of a shade generally near Geranium Lake 20/1 (or darker) on the top surface and yellowish to pink on reverse, the bud and flower resembling the variety Over The Rainbow (U.S. Plant Pat. No. 3,472) in form and size but deeper in color; and further characterized by a plant of vigorous and compact growth habit, easy to propagate from cuttings, with an abundance of flowers borne usually one to the stem.

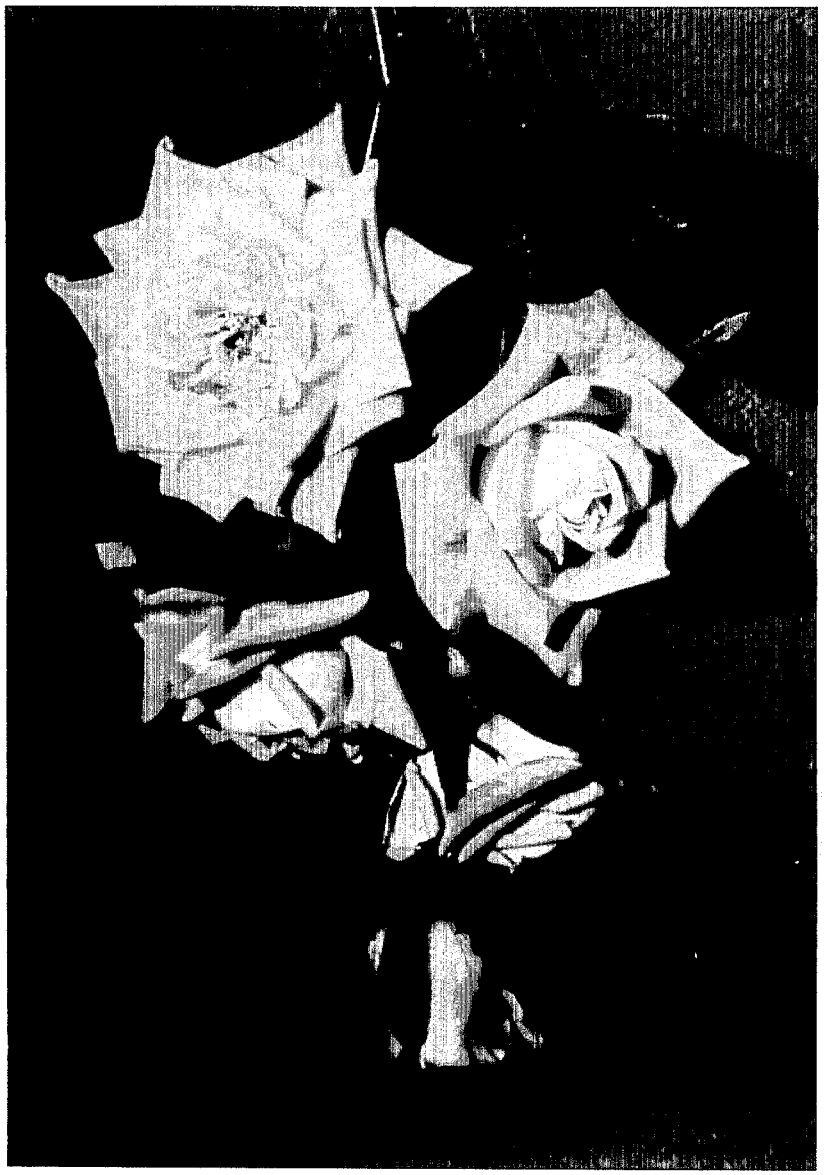

* * * * *